(12) United States Patent
Kim et al.

(10) Patent No.: US 10,048,251 B2
(45) Date of Patent: Aug. 14, 2018

(54) SINGLE-PAD STRIP FOR AN IMPROVED LATERAL FLOW ASSAY AND A TEST DEVICE USING THE SAME

(71) Applicant: ACCESS BIO, INC., Somerset, NJ (US)

(72) Inventors: Hyeon Suk Kim, Dayton, NJ (US); Tae-Hee Koo, Somerset, NJ (US); Young Ho Choi, Princeton, NJ (US)

(73) Assignee: ACCESS BIO, INC., Somerset, NJ (US)

( * ) Notice: Subject to any disclaimer, the term of this patent is extended or adjusted under 35 U.S.C. 154(b) by 0 days.

(21) Appl. No.: 15/438,286

(22) Filed: Feb. 21, 2017

(65) Prior Publication Data

US 2017/0199177 A1    Jul. 13, 2017

Related U.S. Application Data

(62) Division of application No. 13/554,417, filed on Jul. 20, 2012, now Pat. No. 9,575,056.

(60) Provisional application No. 61/510,762, filed on Jul. 22, 2011.

(51) Int. Cl.
  *G01N 33/52* (2006.01)
  *C12Q 1/32* (2006.01)
  *G01N 33/98* (2006.01)

(52) U.S. Cl.
  CPC .............. *G01N 33/526* (2013.01); *C12Q 1/32* (2013.01); *C12Y 101/01027* (2013.01); *C12Y 101/01049* (2013.01); *G01N 33/98* (2013.01); *G01N 2333/904* (2013.01)

(58) Field of Classification Search
  None
  See application file for complete search history.

(56) References Cited

U.S. PATENT DOCUMENTS

2004/0203086 A1 * 10/2004 Piasio .............. G01N 33/54326
                                                     435/11
2011/0124851 A1 * 5/2011 Guo .................... C12N 15/1006
                                                     536/23.1

FOREIGN PATENT DOCUMENTS

WO     WO-0222855 A2 *   3/2002   ........... G01N 33/523

* cited by examiner

*Primary Examiner* — Paul J Holland
(74) *Attorney, Agent, or Firm* — Lucas & Mercanti, LLP

(57) ABSTRACT

The present invention relates to a strip for an improved lateral flow assay of a biological sample on a single plane and a lateral flow chromatography assay using a test device containing the same. The strip of the present invention consists of a single-pad, which can improve lateral flow assay by providing an easy and simple procedure and clear visual reading. The strip of the present invention is consisted of sample application (sample) zone and reactant-resultant zone where the reaction mixture is deposited (reactant) are all on a same plane. In addition, the present invention provides a chromatographic method wherein hemoglobin is separated from analyte by a differential chromatography on the solid phase. Any interference of detection of the result by hemoglobin is removed by the present invention. The present invention provides advantages including an easy and simple procedure with a quick and clear response.

10 Claims, 8 Drawing Sheets

A. One Pad System

B. Two Pads System

Color intensity:
    0. No Color
    1. Barely visible
    2. weak purple
    3. moderate purple
    4. strong purple
    5. very strong purple

- One pad system: Strong purple color
- Two pad system: migration of blood is slower than one pad system and weak purple color is developed.

Color intensity:
   0. No Color
   1. Barely visible
   2. weak purple
   3. moderate purple
   4. strong purple
   5. very strong purple

SINGLE-PAD STRIP FOR AN IMPROVED LATERAL FLOW ASSAY AND A TEST DEVICE USING THE SAME

CROSS-REFERENCE TO RELATED APPLICATIONS

This application is a divisional application of U.S. patent application Ser. No. 13/554,417, filed Jul. 20, 2012, now U.S. Pat. No. 9,575,056 B2, issued Feb. 21, 2017, which claims the benefit of priority from U.S. Provisional Patent Application Ser. No. 61/510,762, filed Jul. 22, 2011, the contents of each of which are incorporated herein by reference.

FIELD OF THE INVENTION

The present invention relates to a single-pad based strip for an improved lateral flow assay of a biological sample and a test device using the same.

BACKGROUND OF THE INVENTION

Tests performed at the point of care (POC) have become common and very useful diagnostic tools not only in health care facilities including hospitals and doctors' offices but also in other clinical sites including workplaces or remote field sites. Due to the urgency and purpose of the testing, a simple and efficient testing device and method to acquire results in cost and time efficient manner is greatly desirable. More specifically, test in non-health care facilities such as in remote field clinical sites testing for fast-growing epidemic disease, testing for bio-warfare agents in the battlefield, environmental testing for pollutants, or workplace testing for drug abuse needs to be performed simply and easily. Sometimes, since these tests are often performed by individuals having little, if any, clinical diagnostics training, these point of care tests need to be simple, quick, and easy to use. Furthermore, the devices are needed in an environment without much control of storage conditions such as temperature or humidity. Thus, the device for the point of care tests ideally requires a minimal amount of equipment and the testing method embedded within the device would be desirable if stable to the harsh environment conditions including temperature or humidity.

With the increased need for point of care tests for increased number of purpose and variant environment, there still is a need in the art to provide a method and a device for performing the test for a biological specimen with cost and time efficient manner.

SUMMARY OF INVENTION

In one embodiment, the present invention provides a single-pad based strip for a lateral flow assay wherein sample application (sample) zone and reactant-resultant zone where the reaction mixture is deposited (reactant) are all on a same plane, a single, one-pad.

In another embodiment, the present invention provides a strip for an enzyme-driven, lateral chromatographic flow assay for a preselected analyte consisting of:
 a single-pad; and
 a substrate deposited as dry form.

In yet another embodiment, the present invention provides an enzyme-driven, lateral chromatographic flow assay for a preselected analyte comprising:

(a) providing a testing device comprising a strip consisting of:
 (i) a single-pad; and
 (ii) a substrate deposited as dry form;
(b) applying a sample to the single-pad wherein the substrate is deposited;
(c) allowing the sample to flow through the digestive pad to reach the substrate;
(d) allowing the sample reacts with the substrate to produce a response; and
(e) identifying and interpreting the response to indicate the presence or concentration of the analyte in the sample.

In further embodiment, the present invention provides an enzyme-driven, lateral chromatographic flow assay for detecting a presence of glucose-6-phosphate dehydrogenase (G6PD) comprising:

(a) providing a test device comprising a single-pad strip comprising:
 (i) a digestive single-pad pre-treated with a lysing buffer;
 (ii) an assay mixture comprising glucose-6-phosphate, nicotinamide adenine dinucleotide phosphate (NADP) or nicotinamide adenine dinucleotide (NAD), hydride or electron transfer agent, and a mixture thereof; and
 (iii) a tetrazolium salt,
(b) applying a sample on the digestive single-pad;
(c) allowing the sample to flow through the digestive pad to contact the assay mixture;
(d) allowing the sample reacts with the assay mixture to produce a response; and
(e) identifying and interpreting the response to indicate the presence or concentration of the analyte in the sample.

In another embodiment, the present invention is based on dry format assay wherein the sample applied in the sample application zone travels to the reaction zone by capillary force while the application zone and the reaction zone are on a same plane. The reactant contains combination of components including enzyme and a composition to elicit color reaction and deposited as dry form. In the present invention, the sample travels to the reactant zone and mixed with reactant. As the sample is mixed with the reactant, the resulting composition will migrate slowly and remain on the reactant-resultant zone, while other components in the sample, such as hemoglobin, move faster than the resulting composition and continue to travel to separate from the desired resultant by such as capillary force. Upon reacting with a sample containing the analytes, the reactant-result zone will present the result in an indicator, such as color. The retention of the resultant and continuing capillary movement of the other component of the sample will remove any interference by the other components, such as hemoglobin, and improve the identification of the result. The sample travels by the capillary force in a liquid contained in the sample, such as blood, or a buffer solution which is additionally applied with the sample.

In one embodiment, the present invention provides a rapid diagnostic test (RDT) in dry format assay on one-pad strip for point of care test. The lateral chromatography on one pad provides a stable test, simple process and fast test result.

In another embodiment, the present invention provides a chromatographic method wherein hemoglobin is separated from analyte using differential chromatography on the solid phase. The color of hemoglobin often interferes visual reading of color reaction of analyte in red blood cell. The present invention provides a lateral chromatographic method wherein the differential migration of samples occurs due to size difference, viscosity, precipitation of analyte with reactant, charge difference through porous matrix impregnated with reagents that will interact with the analyte.

Advantage of the invention includes the capability of easy and simple procedure, and clear visual reading free from the interference of hemoglobin.

Throughout this application, the following terms have the meanings set forth below.

"Biological material," "biological sample" or "sample" refers to fluid or tissue extracted from vertebrates, such as whole blood, serum, plasma, saliva, urine, and cerebral spinal fluid.

"Analyte" refers to a certain component in a biological material, biological sample, or sample which contains a specific activity which is the purpose of the assay to identify one of the results such as presence, absence, or concentration.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent application, patents, and other references mentioned herein are incorporated by reference in their entirety. In the case of conflict, the present specification, including definitions will control. In addition, the materials, methods, and examples are illustrative only and not intended to be limiting.

Other features and advantages of the invention will be apparent from the following detailed description, and from the claims.

DETAILED DESCRIPTION OF INVENTION

Figure 1:
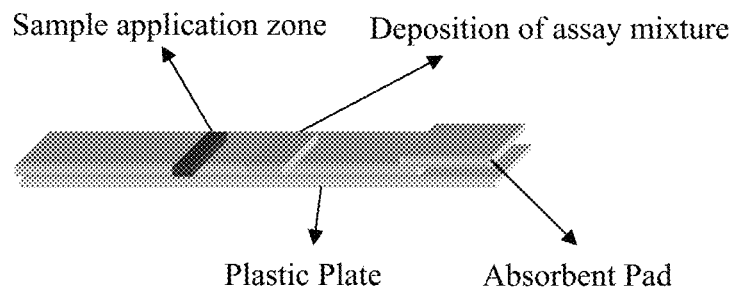
FIG. 1 provides a structure of the one-pad strip of the present invention, compared to conventional two-pad strip.
Figure 1:
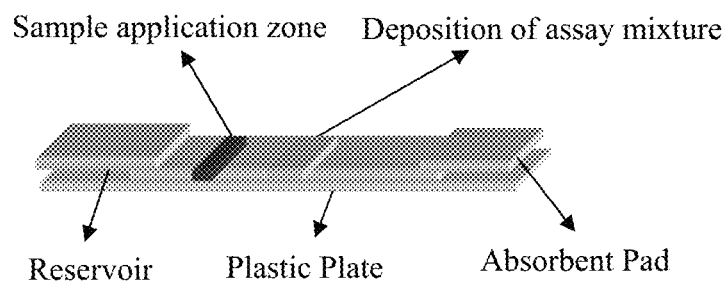
Figure 1:
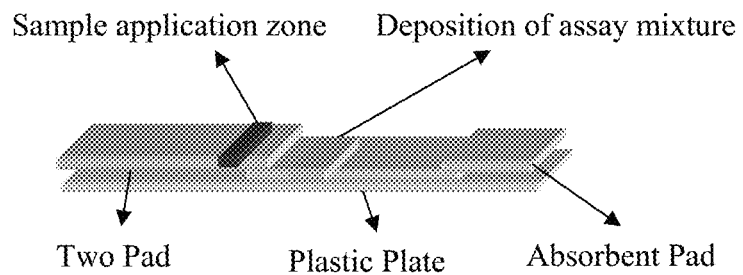

The present invention provides a strip for an enzyme-driven, lateral chromatographic flow assay for a preselected analyte consisting of:
a single-pad; and
a substrate deposited as dry form.

In one embodiment, the single-pad of the present invention is a digestive pad pre-treated with a lysing buffer, such as magnesium chloride.

In another embodiment, the analyte is selected from among protein, carbohydrate, lipid, nucleic acid in the human and animal fluid.

In another embodiment, the substrate deposited as dry form is an assay mixture containing a reactive substrate for the analyte, such as glucose-6-phosphate for glucose phosphate dehydrogenase (G6PD), which can further comprises nicotinamide adenine dinucleotide phosphate (NADP), hydride transfer agent, and a mixture thereof.

In certain embodiment, the analyte is selected from among glucose-6-phosphate dehydrogenase (G6PD), lactate dehydrogenase, or alcohol.

In one preferred embodiment, the analyte is glucose-6-phosphate dehydrogenase (G6PD).

In further embodiment, the substrate contains an indicator such as a dye compound. Many compounds, which can be altered, electronically or structurally, by the contact of the substrate the analyte, and express the change in any form detectable visually or using a measurement method or instrument can be employed without limitations. Examples of such compounds include but not limited to a dye. Compounds expressing various colors often change the color by any chemical or electron status alteration in the structure. Formazan dyes are chromogenic compounds produced from a reduction of tetrazolium salts by dehydrogenases and reductases. Formazan dyes have a variety of colors from dark blue to deep red to orange, depending on the original tetrazolium salt used as the substrate for the reaction. A list of tetrazolium salts includes, but not limited, TTC (tetrazolium, tetrazolium chloride or 2,3,5-triphenyl-2H-tetrazolium chloride), INT (2-(4-Iodophenyl)-3-(4-nitrophenyl)-5-phenyl-2H-tetrazolium chloride), MTT (3-(4,5-dimethyl-2-thiazolyl)-2,5-diphenyl-2H-tetrazolium bromide), XTT (2,3-bis-(2-methoxy-4-nitro-5-sulfophenyl)-2H-tetrazolium-5-carboxanilide), NBT (Nitroblue Tetrazolium), MTS (3-(4,5-dimethylthiazol-2-yl)-5-(3-carboxymethoxyphenyl)-2-(4-sulfophenyl)-2H-tetrazolium), or DCPIP (2,6-dichlorophenolindophenol). Some tetrazolium salts are more water soluble than others. Upon reduction by either enzyme or chemical condition such as reacting with nicotinamide adenine dinucleotide hydride (NADH) or nicotinamide adenine dinucleotide phosphate (NADPH) or any hydride transferring agent, tetrazolium salt can turn color and may even form an insoluble precipitate. The result can be detected by methods, such as but not limited by visual inspection, colorimeter, UV detector, spectrophotometer, image analysis reader, etc.

In one embodiment, the present invention provides an enzyme-driven, lateral chromatographic flow assay for a preselected analyte comprising:

(a) providing a testing device comprising a strip consisting of:
 (i) a single-pad; and
 (ii) a substrate deposited as dry form;
(b) applying a sample to the single-pad wherein the substrate is deposited;
(c) allowing the sample to flow through the digestive pad to reach the substrate;
(d) allowing the sample reacts with the substrate to produce a response; and
(e) identifying and interpreting the response to indicate the presence or concentration of the analyte in the sample.

In one preferred embodiment, the analyte is an enzyme such as G6PD.

In another preferred embodiment, the present invention provides an enzyme-driven, lateral chromatographic flow assay for detecting a presence of G6PD comprising:
(a) providing a test device comprising a single-pad strip comprising:
 (i) a digestive single-pad pre-treated with a lysing buffer;
 (ii) an assay mixture comprising glucose-6-phosphate, nicotinamide adenine dinucleotide phosphate (NADP), or nicotinamide adenine dinucleotide (NAD), hydride transfer agent, and a mixture thereof; and
 (iii) a tetrazolium salt;
(b) applying a sample on the digestive single-pad;
(c) allowing the sample to flow through the digestive pad to contact the assay mixture;
(d) allowing the sample reacts with the assay mixture to produce a response; and
(e) identifying and interpreting the response to indicate the presence or concentration of the analyte in the sample.

The present invention provides a lateral flow assay wherein sample application (sample) zone and reactant-resultant zone where the reaction mixture is deposited (reactant) are all on a same plane, a single, one pad.

In addition, the present invention is based on dry format assay wherein the sample applied in the sample application zone travels to the reaction zone by capillary force while the application zone and the reaction zone are on a same plane. The reactant contains combination of components including enzyme and a composition to elicit color reaction and deposited as dry form. In the present invention, the sample travels to the reactant zone and mixed with reactant.

As the sample is mixed with the reactant, the resulting composition will precipitate, move slowly and remain on the reactant-resultant zone, while other components in the analyte, such as hemoglobin, continue to travel to separate from the desired resultant by such as capillary force. Upon reacting with sample containing analyte, the react-result zone will present the result with an indicator, such as color, which can be visually detected. At the same time, the reverse reading is also possible: Upon reacting with a sample containing analyte the react-result zone with an indicator, such as color, would disappears. Sample containing no analyte: color stays at result zone) The retention of the resultant and continuing capillary movement of the other component of the sample will remove any interference by the other analyte, such as hemoglobin, and improve the identification of the result. The sample travels by the capillary force in a liquid contained in the sample, such as blood, or a buffer solution which can be additionally applied with the sample.

One-Pad Strip

The present invention provides a one-pad strip device, wherein the sample application zone and reactant-result zone are all on one pad. The assay performed in a single pad will provide uniform migration of analytes and produce consistent results by eliminating the uneven migration of sample through multiple layers. For example, when a blood sample is applied to the one pad strip which is pretreated with lysing buffer, hemoglobin can be easily separated from the resultant.

In addition, sensitivity can be increased in the one-pad strip device by increasing actual amount of analyte reacting with reactant than the amount of analyte, as the sample will travel through the same surface instead passing through different media or layers. Also, by employing the one-pad strip device, the production cost will be lower and process will be simpler than that of conventional multi-layer assay.

For example, BinaxNOW® G6PD test has a strip that consists of two different pads which are a sample pad and a reaction pad. Samples with normal G6PD activity produce a distinct color change. The red sample color changes to a brown/black color on the upper half of the reaction pad. The color of the reaction product in blood sample does not eliminate the color of hemoglobin; consequently the brown/black color does not have a clear difference from the red-color of blood. Unlike the bi- or multi phase and discontinuous system used in other devices including Binax-NOW® G6PD, the present invention employs a single phase and continuous chromatography. The test strip consists of a single pad and the continuous chromatography provides an easier separation of resultant with a dye, such as formazan dye, from hemoglobin on the strip than two phase chromatography.

The present invention consists of three areas, sample application (sample) zone, reactant and resultant zone. The reaction zone is the area that the combination of component to elicit color reaction is deposited as dry form and the resultant zone is a visual reading area and the sample zone is an area that sample is applied to. Because these zones are comprised of the same matrix, the one-pad, continuous format which enables uniform migration of analyte and produces consistent results by eliminating the possibility of uneven migration of sample through multiple layers. In addition, sensitivity can be increased by increasing actual amount of analyte reacting with reactant than the amount of analyte passing through the multilayer. Also, the format of this invention lower product cost and makes product process easier than that of conventional multi-layer assay.

Lateral Flow Chromatographic Assay

The analyte reacts with the reactant using various reactions, such as immunological reaction between antibody-antigen reaction, enzyme-substrate reaction, protein-substrate conjugation, or substrate-substrate complex formation.

While the immunological assays have utilized a lateral flow chromatographic assay often, the lateral flow chromatographic assay has not been employed as common for enzymatic assay. A lateral flow enzyme assay identifies a certain enzyme for its presence or absence and the concentration using a reaction with a substrate and detecting the reaction using an indicator such as dye, which can express certain color upon reacting with a certain chemical, such as hydride, produced by the reaction between the enzyme and the substrate.

Glucose-6-Phosphate Dehydrogenase (G6PD)

One specific embodiment of the present invention provides an enzyme based assay, such as direct detection of presence of an enzyme in the sample, such as G6PD in a blood sample, utilizing the activity of the metabolite from the reaction between enzyme and its substrate which can reduce a dye to express certain indicators such as color. Dye molecule, such as tetrazolium compound can be reduced to form an insoluble formazan. The insoluble formazan will present a purple color which can be easily identified visually without any specific equipment.

A human enzyme glucose-6-phosphate dehydrogenase (G6PD) performs a critical function in human biochemistry. It is part of the oxidative pentose pathway, wherein it functions to minimize oxidative attacks of free radicals upon cells by providing reducing equivalents. For example, G6PD converts glucose-6-phosphate to 6-phosphoglutonate, thereby, releasing a proton that reduces nicotinamide adenine dinucleotide phosphate (NADP) to NADPH, a reduced form of NADP. The NADPH initiates a series of downstream reactions that ultimately reduce the free radical oxidizing agents and render many of them ineffective in normal human biochemistry.

G6PD is present in most human cells, but it is in higher concentration in red blood cells which, in one of their primary function, act as oxygen transporter and are therefore particularly susceptible to oxidative attack. This enzyme helps protect red blood cells from oxidative damage and premature destruction. The efficiency of the G6PD system is remarkably high as reflected by the fact that, during normal activity, less than 1% of its capacity is utilized in combating and preventing undesirable oxidative reactions. However, when strong oxidizing agents, such as members of the quinine class of anti-malarial drugs must be introduced to human body, the need for rapid production of reducing agent is greatly increased.

Several mutations of the gene, which encodes for G6PD are known, which decrease the efficiency of the enzymes in the biochemistry of individuals processing such a mutation in both halves of their genome, causing the quantity of their G6PD to remain at the same level as in people with a normal gene, but also causing their G6PD to show greatly reduced specific activity. In these individuals, administration of strong oxidizing agents such as members of the class of quinine-type anti-malarial drug may cause severe clinical complications, such as hemolytic anemia, because the low specific activity of their G6DP does not enable the production of sufficient reducing agents to prevent rapid unwanted oxidative effects on their red blood cells. In areas where malarial infections are common and at times even epidemic, a need therefore exists for a rapid efficient test that will readily distinguish persons having G6PD of low specific activity from persons whose G6PD activity is normal and will enable medical personnel to ensure that (1) the quinine anti-malarial drugs are prescribed only for individuals with normal or better G6PD specific activity and (2) persons with lower than normal G6PD activity are medicated with an alternative type of anti-malarial drugs.

In addition, various types of drugs are known to increase hemolytic anemia and the list includes, but not limited, antimalarials (primaquine, pamaquine, etc.), sulfonamides (sulphanilamide, sulphacetamide, sulphapyridine, sulphamethoxazole, etc.), sulfones (dapsone, etc.), nitrofurans (nitrofurantoin, etc.), and others (nalidix acid, naphthalene, ciprofloxacin, methylene blue, toluidine blue, etc.).

To test the deficiency of G6PD, the red-blood cells containing glucose-6-phosphate dehydrogenase (G6PD) is lysed onto the test strip when it comes into contact to the sample application zone pre-treated with blood lysing reagent. The G6PD in a lysed red-blood cell reacts with its substrates in the pre-treated dry strip, and the enzyme reaction occurs to initialize the color forming process in the presence of a tetrazolium dye and a hydride transfer agent. The catalyzed G6PD can oxidize the glucose-6-phosphate to release NADPH and the released NADPH reduces the tetrazolium dye to change the color of tetrazolium dye to formazan, such as purple or blue, etc., which can be detected visually on the same pad.

In one specific embodiment, the test strip is constructed in a single layer which sample application and color-forming reaction area are on the same pad. The top of the test strip is comprised of an absorbent pad with bibulous material, if needed. The test strip is pre-treated with lysing reagent including ionic or non-ionic surfactants. It provides simple procedure to perform the test as it has no requirement of blood-lysis step before application of sample. The pre-treated test strip is impregnated by reagents comprising: glucose-6-phosphate which is a specific substrate of G6PD, coenzymeNADP or NAD, tetrazolium dye, and hydride transfer agent and stabilizer as sugar moiety or water soluble polymer.

Rapid Diagnostic Test (RDT) and Dual Testing

In one embodiment, the present invention provides a rapid diagnostic test (RDT) in dry format assay on one-pad strip for point of care test. The dry format lateral chromatography provides a stable test device, simple process and fast test result. G6PD deficiency is one of the most common human enzyme deficiency affecting 400 million people and highly prevalent in malaria endemic areas. This deficiency appears to provide some protection from malaria infection. However, it also can cause hemolysis upon administration of certain malarial drugs, including PRIMAQUINE. Therefore, there is an urgent need of rapid diagnostic test (RDT) suitable for the field to screening.

In another embodiment, the present invention provides a test method wherein the G6PD RDT test results using clinical samples can correlate with the quantitative test results. The test can detect about ≤4 IU/gHb (normal 12±2.09 U/gHb at 37° C.) as deficient. The cutoff can be altered depending on the tolerance of red blood cells against PRIMAQUINE in G6PD deficient patient. Accelerated stability studies provided that test strips were stable for three months at 45° C. and 10 days at 60° C. This RDT for G6PD can be combined with a RDT for malaria which is capable of detecting less than 30 parasites per µL of blood. This dual test kit can diagnose malaria infection and G6PD deficiency at the same time using small amount of blood (usually less than 10 µL). The assay test is rapid (<10 minutes) with small quantity of sample (<10 µL of blood), simple to use, cost-effective, portable, and has no special storage requirement which is a critical element for field use.

Lateral Flow Chromatography

Many commonly used point of care tests utilize a lateral flow assay based on membrane-based immuno-chromatography which takes advantage of the capillary action of microporous membranes. In lateral flow chromatographic assays, analytes in the mobile phase specimen solutions are separated from other components by affinity binding to capture molecules on stationary solid phases. Membranes, made of nitrocellulose or nylon, provide a matrix for the solid stationary phase of affinity chromatography and the liquid phase of partition chromatography which drives immunocomplex particles to be separated from other liquid solutes by capillary action.

Microporous membranes, made of nylon or nitrocellulose, have been used for antigen/antibody testing since about 1979 when it was first demonstrated that proteins could be transferred through a membrane. Nitrocellulose has been utilized extensively as a surface for immobilizing proteins in research techniques such as Western blotting and lateral-flow immunodiagnostics. Microporosity and nitrocellulose offer many benefits for rapid immuno-chromatography assays including, for example, high binding capacity, non-covalent attachment of proteins, and a stable long-term immobilization environment.

In general, in the lateral chromatography, including enzyme-driven assays such as a test for G6PD deficiency, the dry substrate is pre-deposited near to and just beyond the junction of the sample receiving area on the chromatographic strip, i.e. one-pad strip as in the present invention. It may, however be placed elsewhere in the sample flow path to accommodate particular requirements of either the sample or one or more ingredients in the substrate, so long as it is placed in the flow path substantially before the end or "absorption pad," where sample flow stops and any excess fluid present runs off into the absorption pad or other sink device that may be provided.

It is important that the dried substrate be deposited in a range, preferably within a confined area, so as to facilitate its being completely picked up by the forward flow of the sample. The placement in the flow path of the dried substrate should also take into consideration that reconstitution of the substrate in dissolved or dispersed form within the liquid sample is desirably completed by the time the sample reaches the point where sample flow ceases.

For convenience of shipping, storage and use, each chromatographic strip of the present invention can be preferably housed within a suitable device constructed so that the strip is positioned laterally. Many such devices are well-known in the art and any of them constructed so that the performance of an assay on the chromatographic strip positioned within it is performed by lateral flow may appropriately be utilized.

In one specific embodiment, the one-pad strip of the present invention provides characteristics, not limited, but including the following:

1. The one-pad strip comprises porous matrix selected from among nitrocellulose membrane, glass fiber, cellulose or polyester etc,
2. The strip comprises a one-pad strip where the sample application area and the deposition area of dried reagent mixture of said strip are in the same pad regardless whether two areas are overlapping or not.
3. The strip in the present invention has a single track of liquid flow to reaction mixture occurs after receiving the sample fluid.
4. The one-pad strip of the present invention can optionally be pre-coated with lysing reagent containing ionic (anionic, cationic and zwitterionic) or non-ionic surfactant and magnesium chloride allowing lysis of biological fluid by contacting to the sample application area directly without pre-lysis with buffer.
5. The one-pad strip of the present invention contains sugar moiety selected from among monosaccharide, disaccharide, polysaccharides or water soluble polymer as a stabilizer to increase thermal stability.
6. The one-pad strip of the present invention are differentially formulated and assembled in a dual testing format device to discriminate moderate (for example: 10-60% of normal activity detection) and severe G6PD deficiency (for example: less than 10% of normal activity detection) by naked eye. % of activity for detection is not limited to 10-60% or less than 10%.
7. The components in the reaction zone comprise enzyme substrates, color-developing reagents and stabilizer. The one pad system can be employed for a quantitative or semi-quantitative assay as the color change on the strip can be readable by instruments, such as optical spectrophotometer, scanner, reader, or densitometer. The
8. One pad system is also applicable to electrochemical system. The electron transfer from NADPH or NADH produced by G6PD to electrode through oxidoreductase or electron transfer mediator can be quantified by using electrode in dry format.
9. The one pad system can be employed for immunoassay which immobilizes capture molecules on the solid phase.

Separation of Hemoglobin from Analyte by Differential Chromatograph

Key parameters controlling signal intensity in lateral chromatography assays are capillary flow rate and protein binding capacity of the membrane. Capillary flow rate and binding capacity are determined by the pore size, porosity, and thickness of the membrane. The protein binding capacity of the membrane depends upon its pore size, and surface properties.

The present invention provides a chromatography wherein hemoglobin is separated from analyte using differential chromatography on the solid phase. The color of hemoglobin often interferes visual reading of color reaction of analyte in red blood cell. The present invention provides a lateral chromatograph method wherein the different migration of samples due to size difference, viscosity, precipitation of analyte with reactant, charge difference through porous matrix impregnated with reagents that will interact with the analyte. The blood cells are applied on the sample zone which is pretreated with lysing agent for red blood lysis to reaction zone and buffer is applied as needed. Lysed blood cells move to reaction-result zone and are mixed with the reactant, the resulting composition will remain on the reactant-resultant zone, while hemoglobin continues to travel to be separated from the desired resultant by such as capillary force. The separation of hemoglobin will make the result detection by an indicator such as color clearer and easier to identify.

EXAMPLE

Figure 2:
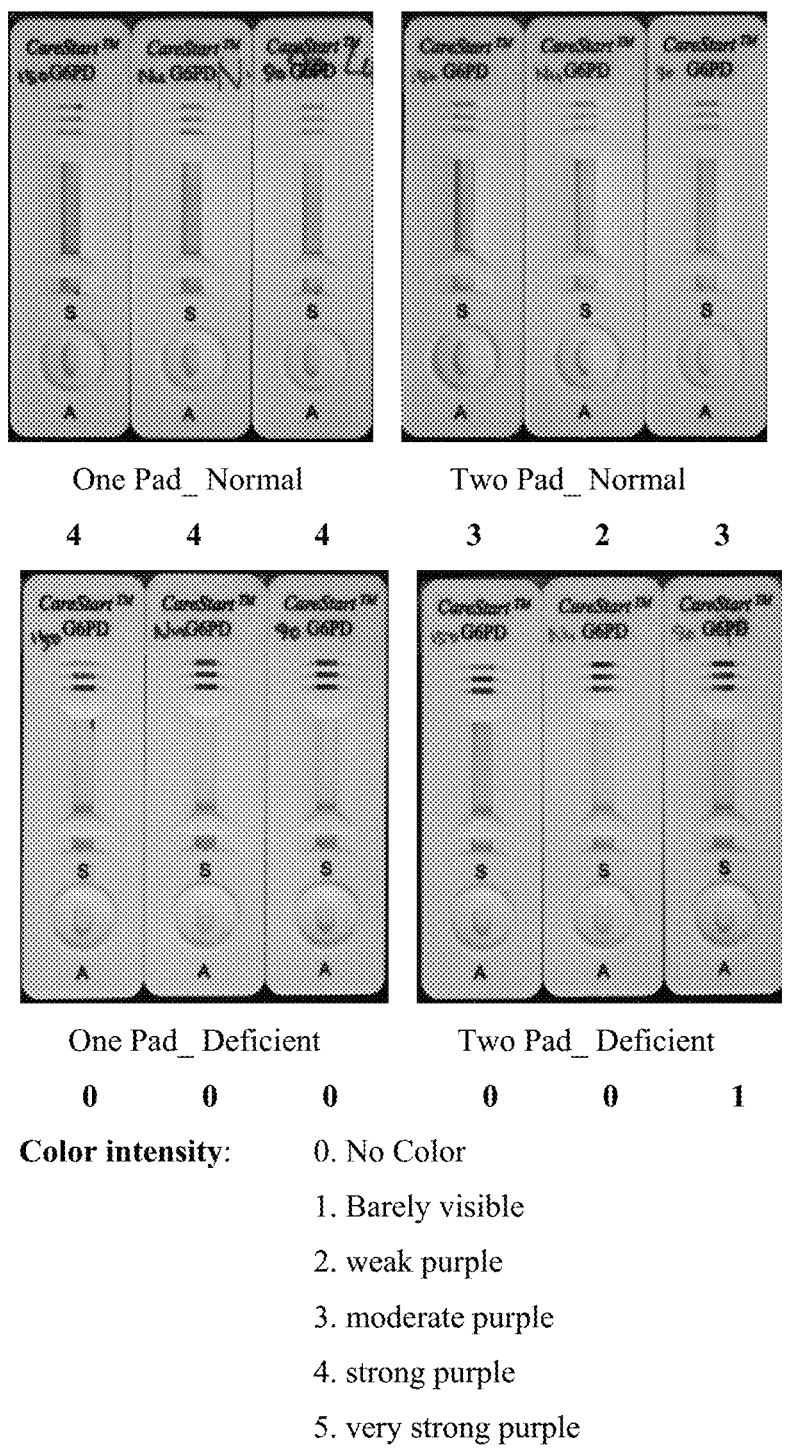
FIG. 2 provides visual comparison test results between the one-pad strip of the present invention compared to conventional two-pad strip for G6PD deficiency test. The intensity of the visual color identification is measured by the score provided in the figure.
Figure 3:
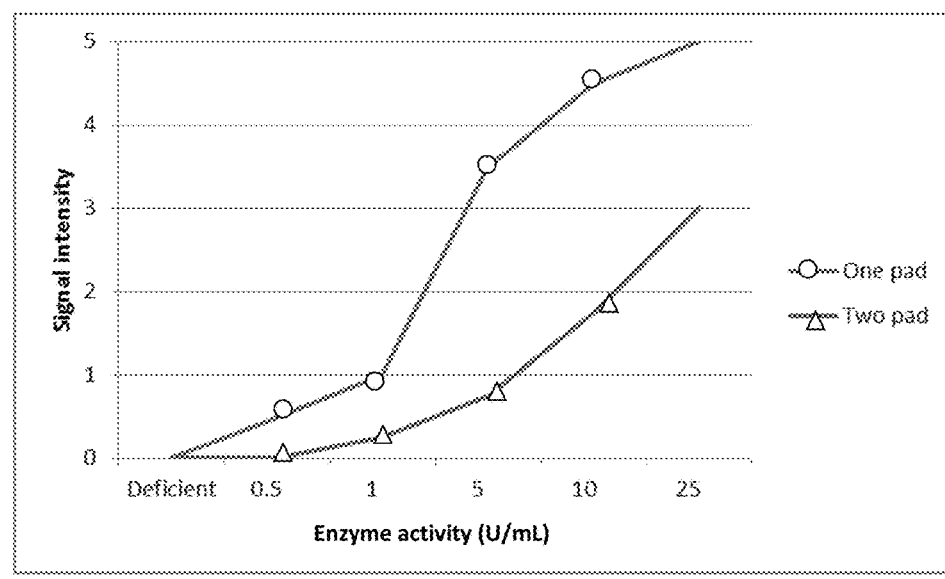
FIG. 3 provides signal intensity comparison test results between the one-pad strip of the present invention compared to conventional two-pad strip using an enzyme assay for G6PD test. The intensity of the visual color identification is measured by the score provided in the figure.

A specific G6PD assay that can easily be used successfully by anyone operating in the field, the home, a doctor's office or at any site where trained laboratory personnel and instrumentation are lacking is specifically described hereinafter and the results are provided in the accompanying FIGS. 1-3.

Example 1. Preparation and Conducting Sample Tests for G6PD Deficiency Test Strip The pad was pre-treated with lysing buffer and it was dried at room temperature. The structures of one-pad and two-pad strips are shown in FIG. 1. The pre-treated pad was attached on the plastic supporter and a bibulous paper was overlapped to the pad in heading portion on the plastic supporter as an absorbent pad. The assay mixture containing glucose-6-phosphate, NADP, tetrazolium, and hydride or electron transfer agent was prepared and it was impregnated onto the porous pad. The assay mixture impregnated pad was allowed to dry at room temperature overnight.

Preparation of one pad: The assay mixture-impregnated pad on the plastic supporter.

Preparation of two pads: The pad for sample application is attached to the bottom of the assay mixture—impregnated pad by overlapping 1-2 mm on the plastic supporter.

Normal or Deficient sample was applied onto strip. The result presents that Normal samples certainly produced stronger and clearer purple color in the one-pad strip system of the present invention than that of two pads, as shown in FIG. 2. Deficient sample did not produce any color in both one and two pads as no G6PD is available to produce NADPH. The result additionally presented that fluid migration is more uniform and faster in one pad than two pads and the completion of blood clearance is faster in one-pad strip system of the present invention than that of two pads.

Example 2. Preparation and Conducting Sample Tests for Lactate Dehydrogenase Test Strip The pad was pre-treated with lysing buffer containing magnesium chloride and it was dried overnight at room temperature. The pre-treated pad was attached on the plastic supporter and a bibulous paper was overlapped to the pad in heading portion on the plastic supporter as an absorbent pad. The assay mixture containing lactate, NAD, tetrazolium, and Tris-HCl buffer pH 8.0 hydride transfer agent was prepared and it was impregnated onto the porous pad. The assay mixture impregnated pad was allowed to dry at room temperature overnight.
  Preparation of one pad: The assay mixture-impregnated pad on the plastic supporter.
  Preparation of two pads: The sample pads are attached to the bottom of the assay mixture—impregnated pad by overlapping 1-2 mm on the plastic supporter.

Figure 4:
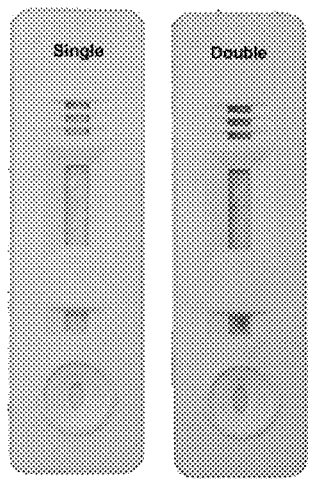
FIG. 4 provides visual comparison test results between the one-pad strip of the present invention compared to conventional two-pad strip for lactate dehydrogenase test.
Figure 5:
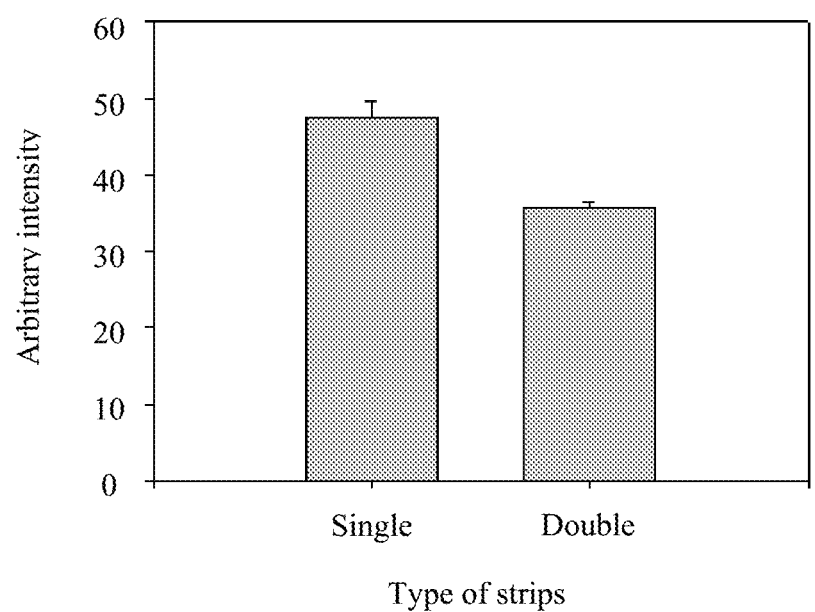
FIG. 5 provides signal intensity comparison test results between the one-pad strip of the present invention compared to conventional two-pad strip using an enzyme assay for lactate dehydrogenase test. The intensity of the visual color identification was measured by an aQzen Reader.

Two micro liter of blood sample was applied onto strip. The result presents that the LDH enzyme in blood certainly produced stronger and clearer purple color in the one pad strip system of the present invention than that of two pads, as shown in FIG. 4. The result additionally presented that fluid migration is more uniform and faster in one pad than two pads and the completion of blood clearance is faster in one-pad strip system of the present invention than that of two pads. The intensity of purple color was measured by aQzen Reader as shown in Table 1. The intensity of one pad is higher than that of two pad system as shown in FIG. 5.

TABLE 1

|  |  | Type of Strip | |
| --- | --- | --- | --- |
|  | # of Exp. | one | two |
| Arbitrary Intensity | $1^{st}$ | 49.51 | 35.79 |
|  | $2^{nd}$ | 47.38 | 36.49 |
|  | $3^{rd}$ | 45.37 | 34.99 |
|  | Average | 47.42 | 35.76 |

Example 3. Preparation and Conducting Sample Tests for Alcohol Test Strip

The pad was pre-treated with buffer containing detergent and it was dried overnight at room temperature. The pre-treated pad was attached on the plastic supporter and a bibulous paper was overlapped to the pad in heading portion on the plastic supporter as an absorbent pad. The assay mixture containing alcohol, NAD, tetrazolium, and Tris-HCl buffer pH8.0, hydride transfer agent was prepared and it was impregnated onto the porous pad. The assay mixture impregnated pad was allowed to dry at room temperature overnight.
  Preparation of one pad: The assay mixture-impregnated pad on the plastic supporter.
  Preparation of two pads: The sample pads are attached to the bottom of the assay mixture—impregnated pad by overlapping 1-2 mm on the plastic supporter.

Figure 6:
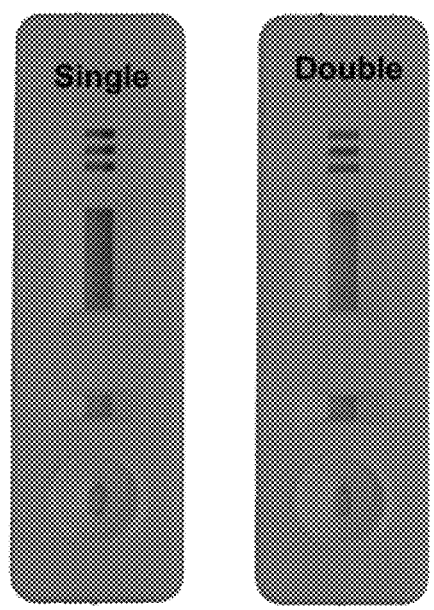
FIG. 6 provides visual comparison test results between the one-pad strip of the present invention compared to conventional two-pad strip for alcohol test.
Figure 7:
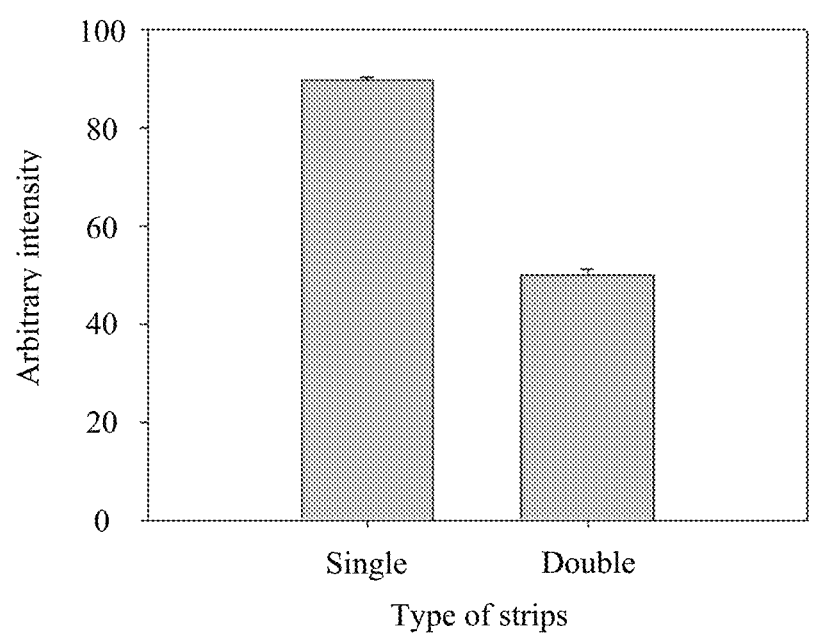
FIG. 7 provides signal intensity comparison test results between the one-pad strip of the present invention compared to conventional two-pad strip using an enzyme assay for alcohol dehydrogenase test. The intensity of the visual color identification was measured by an aQzen Reader.

2 micro liter of blood sample containing alcohol was applied onto strip. The result presents that the presence of alcohol in blood certainly produced stronger and clearer purple color in the one pad strip system of the present invention than that of two pads, as shown in FIG. 6. The intensity of purple color was measured by an aQzen Reader as shown in Table 2. The intensity of one pad is higher than that of two pad system as shown in FIG. 7.

TABLE 2

|  |  | one | two |
| --- | --- | --- | --- |
| Arbitrary Intensity | $1^{st}$ | 89.00 | 48.45 |
|  | $2^{nd}$ | 89.88 | 49.90 |
|  | $3^{rd}$ | 90.42 | 51.00 |
|  | Average | 89.77 | 49.79 |
|  | SD | 0.51 | 0.90 |

Example 4. Preparation and Conducting Sample Tests for Lactate Dehydrogenase Test Strip-Depend on Activity of Lactate Dehydrogenase The pad was pre-treated with buffer containing detergent and it was dried overnight at room temperature. The pre-treated pad was attached on the plastic supporter and a bibulous paper was overlapped to the pad in heading portion on the plastic supporter as an absorbent pad. The assay mixture containing lactate, NAD, tetrazolium, and Tris-HCl buffer pH8.0 hydride transfer agent was prepared and it was impregnated onto the porous pad. The assay mixture impregnated pad was allowed to dry at room temperature overnight.
  Preparation of one pad: The assay mixture-impregnated pad on the plastic supporter.
  Preparation of two pads: The sample pads are attached to the bottom of the assay mixture—impregnated pad by overlapping 1-2 mm on the plastic supporter.

Figure 8:
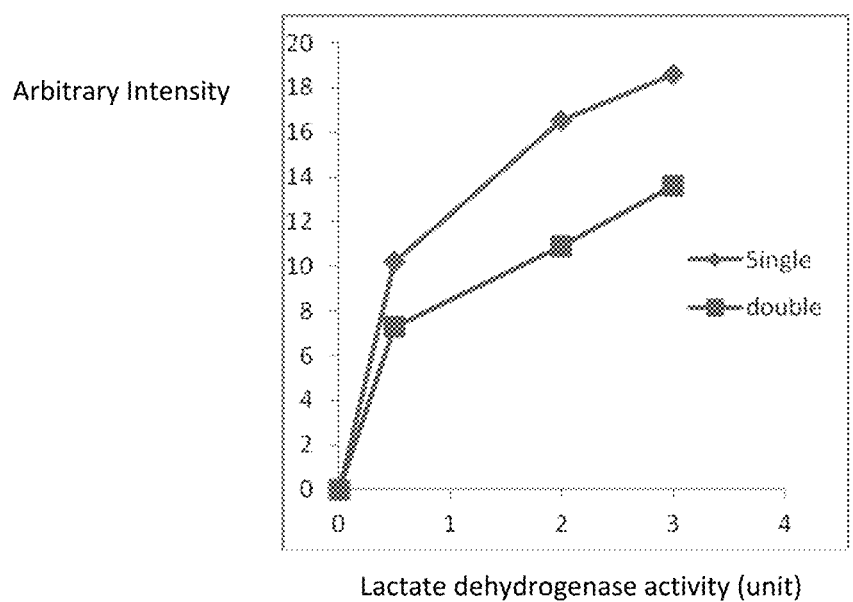
FIG. 8 provides signal intensity comparison test results between the one-pad strip of the present invention compared to conventional two-pad strip using an enzyme assay for lactate dehydrogenase test. The intensity of the visual color identification is measured by the score provided in the figure.

Two micro liter of sample containing lactate dehydrogenase (from 0.5 unit to 6 unit) was applied onto strip. The result presents that the LDH enzyme activity produced stronger and clearer purple color in the one pad strip system of the present invention than that of two pads, as shown in FIG. 8.

We claim:

1. An enzyme-driven, lateral chromatographic flow assay for a preselected analyte comprising the steps of:
  (a) providing a testing device comprising a strip consisting of:
    (i) a single-pad; and
    (ii) a reactant zone impregnated with a dry substrate capable of forming a precipitate when reacted with said preselected analyte:
  wherein:
    said single-pad is pretreated with a blood lysing reagent;
    said strip is capable of separating said preselected analyte or a reaction resultant from hemoglobin present in a blood sample being assayed by differential migration of said preselected analyte or hemoglobin components;
    said hemoglobin components migrate faster than said preselected analyte or said reaction resultant;
    said reaction resultant is a reaction product generated by interaction between said preselected analyte and said dry substrate;

red-blood cells in said blood sample are lysed upon contact with said blood lysing reagent; and said preselected analyte is selected from the group consisting of protein, carbohydrate, lipid, alcohol, and nucleic acid in a human or animal fluid;

(b) applying a sample to said single-pad wherein said dry substrate is deposited;

(c) allowing said sample to flow through said single-pad to reach said dry substrate;

(d) allowing said sample to react with said dry substrate to produce a response; and (e) identifying and interpreting the response to indicate the presence or concentration of said preselected analyte in said sample.

2. The assay of claim 1, wherein said protein is glucose-6-phosphate dehydrogenase (G6PD) or lactate dehydrogenase.

3. The assay of claim 1, wherein said dry substrate is an assay mixture comprising glucose-6-phosphate, nicotinamide adenine dinucleotide phosphate (NADP) or nicotinamide adenine dinucleotide (NAD), hydride or electron transfer agent, and a mixture thereof.

4. The assay of claim 1, wherein said dry substrate comprises an indicator.

5. The assay of claim 4, wherein said indicator is a dye compound.

6. The assay of claim 5, wherein said dye compound is selected from the group consisting of TTC (2,3,5-triphenyl-2H-tetrazolium chloride), INT (2-(4-Iodophenyl)-3-(4-nitrophenyl)-5-phenyl-2H-tetrazolium chloride), MTT (3-(4,5-dimethyl-2-thiazolyl)-2, 5-diphenyl-2H-tetrazolium bromide), XTT (2,3-bis-(2-methoxy-4-nitro-5-sulfophenyl)-2H-tetrazolium-5-carboxanilide), NBT (nitroblue tetrazolium), MTS (3-(4,5-dimethylthiazol-2-yl)-5-(3-carboxymethoxyphenyl)-2-(4-sulfophenyl)-2H-tetrazolium), and DCPIP (2,6-dichlorophenolindophenol).

7. The assay of claim 5, wherein said dye compound is tetrazolium salt.

8. The assay of claim 1, wherein said blood-lysing reagent comprises ionic or nonionic detergents.

9. The assay of claim 1, wherein said differential migration of said preselected analyte or said hemoglobin components results from differences in size, viscosity, charge or solubility, or by differential interaction with reagents embedded in said single-pad.

10. The assay of claim 1, wherein said preselected analyte is in said red-blood cells.

* * * * *